(12) United States Patent
De Meijer

(10) Patent No.: US 9,035,130 B2
(45) Date of Patent: May 19, 2015

(54) REFERENCE PLANT, A METHOD FOR ITS PRODUCTION, EXTRACTS OBTAINED THEREFROM AND THEIR USE

(75) Inventor: Etienne De Meijer, Salisbury (GB)

(73) Assignee: GW Pharma Limited, Salisbury (GB)

( * ) Notice: Subject to any disclaimer, the term of this patent is extended or adjusted under 35 U.S.C. 154(b) by 1597 days.

(21) Appl. No.: 12/156,460

(22) Filed: May 30, 2008

(65) Prior Publication Data

US 2009/0035396 A1 Feb. 5, 2009

Related U.S. Application Data

(60) Provisional application No. 60/932,437, filed on May 31, 2007.

(51) Int. Cl.
*A01H 5/00* (2006.01)
*A61K 36/185* (2006.01)
*A01H 1/00* (2006.01)

(52) U.S. Cl.
CPC ............... *A61K 36/185* (2013.01); *A01H 1/00* (2013.01); *A01H 5/00* (2013.01)

(58) Field of Classification Search
None
See application file for complete search history.

(56) References Cited

FOREIGN PATENT DOCUMENTS

| WO | WO 01/66089 A2 | 9/2001 |
|---|---|---|
| WO | WO 02/064109 A2 | 8/2002 |
| WO | WO 02/089945 A2 | 11/2002 |
| WO | WO 03/037306 A2 | 5/2003 |
| WO | WO 2004/016246 A1 | 2/2004 |
| WO | WO 2004/016277 A2 | 2/2004 |

OTHER PUBLICATIONS

Pacifico D., et al. Molecular Breeding (2006) vol. 17; pp. 257-268.*
Novak, J et al. Flavour and Fragrance Journal 2001; vol. 16, pp. 259-262.*
Vanhoenacker, G et al. Natural Product Letters, vol. 16, No. 1, pp. 57-63.*
Wilkinson, J.D. et al. Journal of Pharmacy and Pharmacology 2003; vol. 55, pp. 1687-1694.*
Small, E. et al. Economic Botany 2003; vol. 57. No. 4; pp. 545-558.*
Hillig, K. W., "A chemotaxonomic analysis of terpenoid variation in *Cannabis*," *Biochem Systematics Ecology* 2004; 32:875-891.
Kriese, U. et al., "Oil content, tocopherol composition and fatty acid patterns of the seed of 51 *Cannabis sativa* L genotypes," *Euphytica* 2004; 137:339-351.
Novak, J. et al., "Essential oils of different cultivars of *Cannabis sativa* L and their antimicrobial activity," *Flavour and Fragrance J* 2001; 16:259-262.
Pacifico, D. et al., "Genetics and Marker-assisted Selection of the Chemotype in *Cannabis sativa* L.," *Molecular Breeding* Apr. 1, 2006; 17(3):257-268.
Small, E. et al., "Tetrahydrocannabinol levels in Hemp (*Cannabis sativa*) germplasm resources," *Economic Botany 1* Jan. 2003; 57(4):545-558.
Vanhoenacker, G. et al., "Chemotaxonomic features associated with flavonoids of cannabinoid-free *Cannabis* in relation to hops", *Natural Product Letts* 2002: 16(1):57-63.
Virovets, V.G. et al., "Selektion auf niedrigen Gehalt der Cannabinoid und hohe Produktivität im Schaffungsprogramm von Hanfsorten (*Cannabis sativa* L.), die kiene narkotische Aktivität besitzen," *Tagungsband Zum/Proceedings of the Symposium Biorohstoff Hanf*, Nova-Institut Für Politische und ÖKologische Innovation; Jan. 1, 1997:135-153.
Wilkinson, J.D. et al., "Medicinal *Cannabis*: is delta-9-tetrahydrocannabinol necessary for all its effects?" *J Pharmacy Pharmacol* 2003; 55:1687-1694.
The United Kingdom Parliament, Select Committee on Science and Technology Ninth Report (1998) at http://www.parliament.the-stationery-office.co.uk/pa/Id199798/ldselect/ldsctech/151/15101.htm.
The United Kingdom Parliament, Select Committee on Science and Technology Second Report (Mar. 14, 2001) at http://www.publications.parliament.uk/pa/ld200001/ldselect/ldsctech/50/5001.htm.
De Meijer, Fibre hemp cultivars: A survey of origin, ancestry, availability and brief agronomic characteristics. J Int Hemp Assoc. 1995;2(2):66-73.
De Zeeuw et al., Cannabinoids with a propyl side chain in cannabis: occurrence and chromatographic behavior. Science. Feb. 18, 1972;175(23):778-9.
Fellermeier et al., Biosynthesis of cannabinoids. Incorporation experiments with (13)C-labeled glucoses. Eur J Biochem. Mar. 2001;268(6):1596-604.
Fellermeier et al., Prenylation of olivetolate by a hemp transferase yields cannabigerolic acid, the precursor of tetrahydrocannabinol. FEBS Lett. May 8, 1998;427(2):283-5.
McPartland et al., *Cannabis* and *Cannabis* extracts: greater than the sum of their parts?. *J Cannabis* Therapeutics. 2001;1:103-32.
Morimoto et al., Enzymological Evidence for Cannabichromenic Acid Biosynthesis. J Nat Prod. Aug. 1997;60(8):854-7.

(Continued)

*Primary Examiner* — Russell Kallis
(74) *Attorney, Agent, or Firm* — Wolf, Greenfield & Sacks, P.C.

(57) ABSTRACT

The invention relates to a reference plant which has been selected to:

a) not express a medicinally active compound or group of compounds; yet b) express, at least substantially qualitatively, most other non medicinally active compounds present in a therapeutically active comparator plant.

The reference plant can be used to generate a reference extract with a reference chemical profile which resembles that of the comparator plant less the active compound or group of compounds and may thus be used as a placebo or to otherwise test the hypothesis that the active compound or compounds are responsible for an extracts perceived medicinal activity.

20 Claims, 7 Drawing Sheets

(56) References Cited

OTHER PUBLICATIONS

Morimoto et al., Purification and characterization of cannabichromenic acid synthase from *Cannabis sativa*. Phytochemistry, Nov. 1998;49(6):1525-9.

Raharjo et al., Cloning and over-expression of a cDNA encoding a polyketide synthase from *Cannabis sativa*. Plant Physiol Biochem. Apr. 2004;42(4):291-7.

Raharjo et al., Olivetol as product of a polyketide synthase in *Cannabis sativa* L. Plant Science. Feb. 2004;166(2):381-5.

Taura et al., First direct evidence for the mechanism of .DELTA.1-tetrahydrocannabinolic acid biosynthesis. J Am Chem Soc. Sep. 1995;117(38):9766-7.

Taura et al., Purification and characterization of cannabidiolic-acid synthase from *Cannabis sativa* L... Biochemical analysis of a novel enzyme that catalyzes the oxidocyclization of cannabigerolic acid to cannabidiolic acid. J Biol Chem. Jul. 19, 1996;271(29):17411-6.

Virovets, Interview. J Int Hemp Assoc. 1998;5:32-4.

Virovets, Selection for Non-Psychoactive Hemp Varieties (*Cannabis sativa* L.) in the CIS (former USSR). J Int Hemp Assoc. 1996;3:13-5.

Samuelsson, Drugs of natural origin, 4th ed. Swedisch Pharmaceutical Press. 1999; 551.

De Meijer et al., The inheritance of chemical phenotype in *Cannabis sativa* L. (II): Cannabigerol predominant plants. Euphytica. 2005;145(1-2):189-98.

Evans, Pharmacognosy $15^{th}$ ed. 2002;585.

Gaoni et al., Cannabichromene, a new active principle in hashish. Chem Comm 1966; 1:20-1.

Gorshkova et al., Methods of evaluating hemp plants for content of cannabinoid compounds. Referativnyi Zhurnal. 1988;12.65.322. Abstract only.

Sirikantaramas et al., Tetrahydrocannabinolic acid synthase, the enzyme controlling marijuana psychoactivity, is secreted into the storage cavity of the glandular trichomes. Plant Cell Physiol. Sep. 2005;46(9):1578-82. Epub Jul. 15, 2005.

Speroni et al., Antiinflammatory effects of *Cannabis sativa* L. extracts containing nonpsychoactive cannabinoids. Borrelli et al. eds. Proceedings $3^{rd}$ International Symposium on Natural Drugs, Indena, Naples. 2003;107-14.

Virovets et al., Narcotic activity of *Cannabis sativa* L. and prospects of its selection for decreased content of cannabinoids. Agricultural Biology 1. 1991;35-49.

Vree et al., Identification of the methyl and propyl homologues of CBD, THC and CBN in hashish by a new method of combined gas chromatography-mass spectrometry. Acta Pharma Suecica. 1971;8:683-4.

Williamson et al., Cannabis as a medicine: evidence for synergy. In Medicinal uses of *Cannabis*, $26^{th}$ LOF Symposium, Leiden 2002.

\* cited by examiner

REFERENCE PLANT, A METHOD FOR ITS PRODUCTION, EXTRACTS OBTAINED THEREFROM AND THEIR USE

RELATED APPLICATION

This application claims the benefit under 35 U.S.C. §119 (e) of U.S. provisional application 60/932,437, filed May 31, 2007, the entire disclosure of which is incorporated herein by reference.

FIELD OF THE INVENTION

The present invention relates to a novel reference plant, a method for producing a novel reference plant, extracts free of a medicinally active compound or group of compounds obtained therefrom and their use. More particularly, the novel reference plant is a plant derived from a comparator plant. In an exemplifying embodiment the medicinal compounds, which are "knocked out", are one or more cannabinoids and the plant is cannabis, *Cannabis sativa*, plant.

BACKGROUND OF THE INVENTION

Many pharmaceuticals are derived from plants and indeed many plants or extracts obtained therefrom are taken as medicines. There are over 120 distinct chemical substances derived from plants that are considered as important drugs that are currently in use. The table below lists some of these substances.

There are many examples of plant-based substances that are known for their medicinal properties. For example a tropical plant, *Cephaelis ipecacuanha*, is known to produce the chemical emetine. A drug was developed from this substance called Ipecac; this was used for many years to induce vomiting. Another example of plant-based substances used as medicines is the plant chemical named taxol found in the Pacific Yew tree. The taxol molecule was produced synthetically to produce the drug PACLITAXEL™, which is used in the treatment of various types of tumours.

The plant substance, cynarin, is a plant chemical found in the common artichoke (*Cynara scolymus*). A cynarin drug is sold for the treatment of liver problems and hypertension. The drug is simply an extract from the artichoke plant that has been standardized to contain a specific amount of cyanarin. Similarly the substance silymarin is a chemical found in the milk thistle plant and natural milk thistle extracts that have been standardized to contain specific amounts of silymarin are also used for the treatment of liver problems.

Some of the drugs/chemicals shown in the table below are sold as plant based drugs produced from processing the plant material. Many plant chemicals cannot be completely synthesised in the laboratory due to the complex nature of the plant extract. For example the tree *Cinchona ledgeriana* produces the substance quinine, which is used in to treat and prevent malaria. Quinine is now chemically synthesised; however, another chemical in the tree called quinidine, which was found to be useful for the treatment of heart conditions, couldn't be completely copied in the laboratory. The tree bark is used to produce a quinidine extract.

The table below details some of the plant-based medicines that are in use today.

| Drug/Chemical | Action/Clinical Use | Plant Source |
| --- | --- | --- |
| Acetyldigoxin | Cardiotonic | *Digitalis lanata* |
| Adoniside | Cardiotonic | *Adonis vernalis* |
| Aescin | Anti-inflammatory | *Aesculus hippocastanum* |
| Aesculetin | Anti-dysentery | *Frazinus rhychophylla* |
| Agrimophol | Anthelmintic | *Agrimonia supatoria* |
| Ajmalicine | Circulatory Disorders | *Rauvolfia sepentina* |
| Allantoin | Wound healing | Several plants |
| Allyl isothiocyanate | Rubefacient | *Brassica nigra* |
| Anabesine | Skeletal muscle relaxant | *Anabasis sphylla* |
| Andrographolide | Baccillary dysentery | *Andrographis paniculata* |
| Anisodamine | Anticholinergic | *Anisodus tanguticus* |
| Anisodine | Anticholinergic | *Anisodus tanguticus* |
| Arecoline | Anthelmintic | *Areca catechu* |
| Asiaticoside | Wound healing | *Centella asiatica* |
| Atropine | Anticholinergic | *Atropa belladonna* |
| Benzyl benzoate | Scabicide | Several plants |
| Berberine | Bacillary dysentery | *Berberis vulgaris* |
| Bergenin | Antitussive | *Ardisia japonica* |
| Betulinic acid | Anticancerous | *Betula alba* |
| Borneol | Antipyretic, analgesic, anti-inflammatory | Several plants |
| Bromelain | Anti-inflammatory, proteolytic | *Ananas comosus* |
| Caffeine | CNS stimulant | *Camellia sinensis* |
| Camphor | Rubefacient | *Cinnamomum camphora* |
| Camptothecin | Anticancerous | *Camptotheca acuminata* |
| (+)-Catechin | Haemostatic | *Potentilla fragarioides* |
| Chymopapain | Proteolytic, mucolytic | *Carica papaya* |
| Cissampeline | Skeletal muscle relaxant | *Cissampelos pareira* |
| Cocaine | Local anaesthetic | *Erythroxylum coca* |
| Codeine | Analgesic, antitussive | *Papaver somniferum* |
| Colchiceine amide | Anti-tumour agent | *Colchicum autumnale* |
| Colchicine | Anti-tumour agent, anti-gout | *Colchicum autumnale* |
| Convallatoxin | Cardiotonic | *Convallaria majalis* |
| Curcumin | Choleretic | *Curcuma longa* |
| Cynarin | Choleretic | *Cynara scolymus* |
| Danthron | Laxative | *Cassia* species |
| Demecolcine | Anti-tumour agent | *Colchicum autumnale* |
| Deserpidine | Antihypertensive, tranquillizer | *Rauvolfia canescens* |
| Deslanoside | Cardiotonic | *Digitalis lanata* |
| L-Dopa | Anti-parkinsonism | *Mucuna* species |
| Digitalin | Cardiotonic | *Digitalis purpurea* |
| Digitoxin | Cardiotonic | *Digitalis purpurea* |
| Digoxin | Cardiotonic | *Digitalis purpurea* |
| Emetine | Amoebicide, emetic | *Cephaelis ipecacuanha* |
| Ephedrine | Sympathomimetic, antihistamine | *Ephedra sinica* |
| Etoposide | Anti-tumour agent | *Podophyllum peltatum* |
| Galanthamine | Cholinesterase inhibitor | *Lycoris squamigera* |
| Gitalin | Cardiotonic | *Digitalis purpurea* |
| Glaucarubin | Amoebicide | *Simarouba glauca* |
| Glaucine | Antitussive | *Glaucium flavum* |
| Glasiovine | Antidepressant | *Octea glaziovii* |
| Glycyrrhizin | Sweetener, Addison's disease | *Glycyrrhiza glabra* |
| Gossypol | Male contraceptive | *Gossypium* species |
| Hemsleyadin | Bacillary dysentery | *Hemsleya amabilis* |
| Hesperidin | Capillary fragility | *Citrus* species |
| Hydrastine | Hemostatic, astringent | *Hydrastis canadensis* |
| Hyoscyamine | Anticholinergic | *Hyoscyamus niger* |
| Irinotecan | Anticancer, anti-tumour agent | *Camptotheca acuminata* |
| Kaibic acud | Ascaricide | *Digenea simplex* |
| Kawain | Tranquillizer | *Piper methysticum* |
| Kheltin | Bronchodilator | *Ammi visaga* |
| Lanatosides A, B, C | Cardiotonic | *Digitalis lanata* |
| Lapachol | Anticancer, anti-tumour | *Tabebuia* species |
| a-Lobeline | Smoking deterrant, respiratory stimulant | *Lobelia inflata* |
| Menthol | Rubefacient | *Mentha* species |
| Methyl salicylate | Rubefacient | *Gaultheria procumbens* |
| Monocrotaline | Anti-tumour agent (topical) | *Crotalaria sessiliflora* |
| Morphine | Analgesic | *Papaver somniferum* |
| Neoandrographolide | Dysentery | *Andrographis paniculata* |

-continued

| Drug/Chemical | Action/Clinical Use | Plant Source |
| --- | --- | --- |
| Nicotine | Insecticide | Nicotiana tabacum |
| Nordihydro-guaiaretic acid | Antioxidant | Larrea divaricata |
| Noscapine | Antitussive | Papaver somniferum |
| Ouabain | Cardiotonic | Strophanthus gratus |
| Pachycarpine | Oxytocic | Sophora pschycarpa |
| Palmatine | Antipyretic, detoxicant | Coptis japonica |
| Papain | Proteolytic, mucolytic | Carica papaya |
| Papavarine | Smooth muscle relaxant | Papaver somniferum |
| Phyllodulcin | Sweetner | Hydrangea macrophylla |
| Physostigmine | Cholinesterase Inhibitor | Physostigma venenosum |
| Picrotoxin | Analeptic | Anamirta cocculus |
| Pilocarpine | Parasympathomimetic | Pilocarpus jaborandi |
| Pinitol | Expectorant | Several plants |
| Podophyllotoxin | Anti-tumour, anticancer agent | Podophyllum peltatum |
| Protoveratrines A, B | Antihypertensive | Veratrum album |
| Pseudoephredrine* | Sympathomimetic | Ephedra sinica |
| Pseudoephedrine, nor- | Sympathomimetic | Ephedra sinica |
| Quinidine | Antiarrhythmic | Cinchona ledgeriana |
| Quinine | Antimalarial, antipyretic | Cinchona ledgeriana |
| Quisqualic acid | Anthelmintic | Quisqualis indica |
| Rescinnamine | Antihypertensive, tranquilliser | Rauvolfia serpentina |
| Reserpine | Antihypertensive, tranquilliser | Rauvolfia serpentina |
| Rhomitoxin | Antihypertensive, tranquilliser | Rhododendron molle |
| Rorifone | Antitussive | Rorippa indica |
| Rotenone | Piscicide, Insecticide | Lonchocarpus nicou |
| Rotundine | Analgesic, sedative, tranquilizer | Stephania sinica |
| Rutin | Capillary fragility | Citrus species |
| Salicin | Analgesic | Salix alba |
| Sanguinarine | Dental plaque inhibitor | Sanguinaria canadensis |
| Santonin | Ascaricide | Artemisia maritma |
| Scillarin A | Cardiotonic | Urginea maritima |
| Scopolamine | Sedative | Datura species |
| Sennosides A, B | Laxative | Cassia species |
| Silymarin | Antihepatotoxic | Silybum marianum |
| Sparteine | Oxytocic | Cytisus scoparius |
| Stevioside | Sweetener | Stevia rebaudiana |
| Strychnine | CNS stimulant | Strychnos nux-vomica |
| TAXOL ® | Anti-tumour agent | Taxus brevifolia |
| Teniposide | Anti-tumour agent | Podophyllum peltatum |
| Tetra-hydrocannabinol | Antiemetic, decrease ocular tension | Cannabis sativa |
| Tetrahydropalmatine | Analgesic, sedative, tranquilizer | Corydalis ambigua |
| Tetrandrine | Antihypertensive | Stephania tetrandra |
| Theobromine | Diuretic, vasodilator | Theobroma cacao |
| Theophylline | Diuretic, bronchodilator | Theobroma cacao and others |
| Thymol | Antifungal (topical) | Thymus vulgaris |
| Topotecan | Anti-tumour, anticancer agent | Camptotheca acuminata |
| Trichosanthin | Abortifacient | Trichosanthes kirilowii |
| Tubocurarine | Skeletal muscle relaxant | Chondodendron tomentosum |
| Valapotriates | Sedative | Valeriana officinalis |
| Vasicine | Cerebral stimulant | Vinca minor |
| Vinblastine | Anti-tumour, Antileukemic agent | Catharanthus roseus |
| Vincristine | Anti-tumour, Antileukemic agent | Catharanthus roseus |
| Yohimbine | Aphrodisiac | Pausinystalia yohimbe |
| Yuanhuacine | Abortifacient | Daphne genkwa |
| Yuanhuadine | Abortifacient | Daphne genkwa |

There are many examples of extracts that are characterized by reference to a supposed active or marker. The principle described herein with reference to *cannabis* plants would thus be applicable to other plant types as are shown in the table above.

As an example of a botanical drug, *Cannabis sativa* has been used as a drug for centuries, although the precise basis for the plants activity is not known. Both THC and CBD, two of the plants cannabinoids, are known to have distinct pharmacological activities and Marinol® (THC) and Sativex® (an extract containing defined amounts of both THC and CBD) are approved products for various medical indications.

In the case of extracts it is of course unclear whether the efficacy of a botanical drug extract is attributable to the identified "active(s)" or "markers" and/or other components present in an extract which may provide an unidentified additive or synergistic effect or in fact be directly responsible for the activity.

In the case of cannabis the supposed actives, the cannabinoids, are produced through a series of enzymatic synthesis which are outlined below:

The first specific step in the pentyl cannabinoid biosynthesis is the condensation of a terpenoid moiety, geranylpyrophosphate (GPP), with the phenolic moiety, olivetolic acid (OA; 5-pentyl resorcinolic acid), to form cannabigerol (CBG). This reaction is catalysed by the enzyme geranylpyrophosphate:olivetolate geranyltransferase (GOT); [1]. Precursors for GPP are the $C_5$ isomers isopentenyl pyrophosphate (IPP) and dimethylallyl pyrophosphate (DMAPP). These compounds can originate from two different pathways:

the mevalonate pathway (MVA) that is located in the cytoplasm; and the deoxyxylulose pathway (DOX) that operates in the plastid compartments.

According to Fellermeier et al. [2], the GPP incorporated into cannabinoids is derived predominantly, and probably entirely, via the DOX pathway of the glandular trichome plastids. The phenolic moiety OA is generated by a polyketide-type mechanism. Rahaijo et al. [3] suggest that n-hexanoyl-CoA and three molecules of malonyl-CoA condense to a $C_{12}$ polyketide, which is subsequently converted into OA by a polyketide synthase.

CBG is the direct precursor for each of the compounds THC [4], CBD [5] and CBC [6], [7] and [8]. The different conversions of CBG are enzymatically catalysed, and for each reaction an enzyme has been identified: THC acid synthase [4] CBD acid synthase [5] and CBC acid synthase [7] and [8].

Cannabinoids with propyl side chains, as identified by Vree et al. [9] and de Zeeuw et al. [10], result if GPP condenses with divarinic acid (DA; 5-propyl resorcinolic acid) instead of OA, into cannabigerovarin (CBGV). The condensation of n-hexanoyl-CoA and two, instead of three, molecules of malonyl-CoA, results in a $C_{10}$ polyketide, which is subsequently cyclisised into DA by a polyketide [11]. The three cannabinoid synthase enzymes are not selective for the length of the alkyl side chain and convert CBGV into the propyl homologues of CBD, THC and CBC, which are indicated as cannabidivarin (CBDV), delta 9-tetrahydrocannabivarin (THCV) and cannabichromevarin (CBCV), respectively [12].

SUMMARY OF THE INVENTION

The above pathway information is provided, as it will assist in an understanding of the probable mechanism—giving rise to the zero cannabinoid plants exemplifying the broader aspects of the invention.

Indeed it would be particularly useful to develop "knock out" plants in which the one or more "actives" or "markers" believed to be characteristic of a plants pharmaceutical activity are not expressed. Such plants would be useful in formulating "true" placebo extracts or comparator extracts for clinical trials and for producing extracts which could be used in pharmacological tests and experiments in order that a better understanding of an extract, and its perceived actives/markers activity.

In the case of *cannabis*, the plant produces a vast array of cannabinoids (including THC and CBD—the main perceived cannabinoid actives) as well as a number of 'entourage' compounds. Entourage compounds are compounds which are related to cannabinoids but have little or no activity at the cannabinoid receptors. Such entourage compounds are thought to behave as modifiers of cannabinoid activity and therefore could enhance pharmacological efficacy. It would be useful to have a plant which did not produce the cannabinoids BUT which produced the entourage compounds and other significant compounds in combinations/amounts which at least substantially qualitatively and preferably also substantially quantitatively resembled that of a comparator plant, i.e. one which chemotypically bears a recognizable resemblance to the medicinal plants used to generate a pharmaceutical or medicine or a nutraceutical or functional food.

According to a first aspect of the present invention there is provided a reference plant which has been selected to:
 a. not express a medicinally active compound or group of compounds; yet express, at least substantially qualitatively, most other non medicinally active compounds present in a therapeutically active comparator plant
 such that the reference plant can be used to generate a reference extract with a reference chemical profile which resembles that of the comparator plant less the active compound or group of compounds and may thus be used as a placebo or to otherwise test the hypothesis that the active compound or compounds are responsible for an extracts perceived medicinal activity.

The term "most other" is taken herein to refer to an amount of non medicinally active compounds expressed by the reference plant which is at least greater than 50% (w/w) of the total compounds in the plant. In specific embodiments the amount is greater than 60% (w/w) non medicinally active compounds, or the amount is greater than 70% (w/w) non medicinally active compounds, or the amount is greater than 80% (w/w) non medicinally active compounds, or the amount is greater than 90% (w/w) non medicinally active compounds, or the amount is greater than 95% (w/w) non medicinally active compounds.

Preferably the reference plant is a *cannabis* plant and the active compound or group of compounds are the cannabinoids.

The cannabis plant is preferably a *Cannabis sativa* plant containing a monogenic mutation that blocks the cannabinoid biosynthesis. Preferably the plant comprises a cannabinoid knock out factor governing a reaction in the pathways towards the phenolic moieties olivetolic and divarinic acid.

Significantly, the reference plant is characterised in that a homogenised bulk extract exhibits a profile of entourage compounds, which is quantitatively substantially similar to that of a reference plant; as for example is shown in FIG. 3.

In one embodiment the homogenised bulk extract has a % v/w oil yield of greater than 0.14%, more preferably greater than 0.2%, through 0.3% to 0.4% or more.

A homogenised bulk steam distilled extract comprises both monoterpenes and sesquiterpines. The monoterpenes comprise detectable amounts of at least myrcene, alpha pinene and beta pinene. Preferably the combined myrcene, alpha pinene and beta pinenes comprise at least 50%, through 60% to at least 70% of the monoterpenes detected. Preferably it will also comprise one or more of limonine and optionally linalool and cis- and/or trans-verbenol.

The sesquiterpenes preferably comprise at least carophyllene and humulene and may further comprise carophyllene oxide.

Preferably humelene epoxide II is not detected in the reference plant.

The reference plants of the invention preferably comprise stalked glandular trichomes. These are present at a density comparable to those present in comparator drug type cannabinoid producing plants. The reference plants typically have small, grey, dull trichomes of various shapes (FIG. 2*a*). Some trichomes comprise headless; pinhead and/or shrivelled trichomes, which may be, flat, convex or concave. They are also free of white trichome heads.

The reference plant may be further characterized in that it expresses monoterpenes, diterpenes, carotenoids, phytol and tetraterpenes. It additionally expresses sesquiterpenes, sterols and triterpenes.

The reference plant is further characterized in that it exhibits branching characteristic of a drug producing phenotype as opposed to a fibre producing phenotype and vigour, characterized in that the total above ground dry weight is comparable to drug producing phenotypes.

According to a further aspect of the present invention there is provided a method of producing a reference plant which does not express a medicinally active compound or group of compounds yet express, at least substantially qualitatively, most other non medicinally active compounds present in a therapeutically active comparator plant comprising:
 a) Selecting a plant which does not express a medicinally active compound or group of compounds;
 b) Selecting a therapeutically active comparator plant; and
 c) Crossing the plant which does not express a medicinally active compound or group of compounds with the therapeutically active comparator plant to obtain an F1 progeny and self-crossing the F1 progeny to obtain an F2 progeny which is selected for the characteristics sought.

According to yet a further aspect of the present invention there is provided an extract obtainable from a reference plant of the invention.

According to yet a further aspect of the present invention there is provided an extract obtainable from a reference plant of the invention. Such extracts may be prepared by any method generally known in the art, for example by maceration, percolation, vaporisation, chromatography, distillation, recrystallisation and extraction with solvents such as C1 to C5 alcohols (ethanol), Norflurane (HFA134a), HFA227 and supercritical or subcritical liquid carbon dioxide. In particular embodiments the extracts may, for example, be obtained by the methods and processes described in International patent application numbers WO02/089945 and WO 2004/016277, the contents of which are incorporated herein in their entirety by reference.

In one embodiment the extract is used or formulated as a placebo. In particular embodiments such formulations and/or placebos may, for example, be formulated as described International patent application numbers WO01/66089, WO02/064109, WO03/037306 and WO04/016246, the contents of which are incorporated herein in their entirety by reference.

According to a further aspect of the present invention there is provided a method of testing a hypothesis that one or more compounds present in a plant extract are responsible or are solely responsible for the extracts pharmacological activity comprising:
 i) selecting a plant according to the first aspect of the invention;
 ii) obtaining an extract therefrom; and iii) running comparative tests against the extract obtained from a comparator plant.

According to a further aspect of the present invention there is provided a method of producing a designer plant extract comprising the steps of:
i) selecting an extract obtainable from a reference plant according to the first aspect of the invention and
ii) combining the extract of (i) with one or more medicinally active components.

By "designer plant extract" is meant a plant extract which includes one or more medicinally active components which do not naturally occur in the reference plant of part i).

In specific embodiments, the medicinally active components may be purified naturally occurring compounds, synthetic compounds or a combination thereof. In a specific embodiment the medicinally active components may be present in a plant extract. This plant extract may be an extract from a "drug producing" plant of the same species as the reference plant of part i). Typically this drug producing plant will not be the comparator plant to the reference plant of part i).

The invention is further described, by way of example only, with reference to novel *Cannabis sativa* plants (and not specific varieties), which do not express cannabinoids but which otherwise, resemble, chemotypically, medicinal *cannabis* plants.

BRIEF DESCRIPTION OF THE DRAWINGS

The invention will be further described, by way of example only to the following figures in which.

DETAILED DESCRIPTION OF THE INVENTION

Figure 1A:
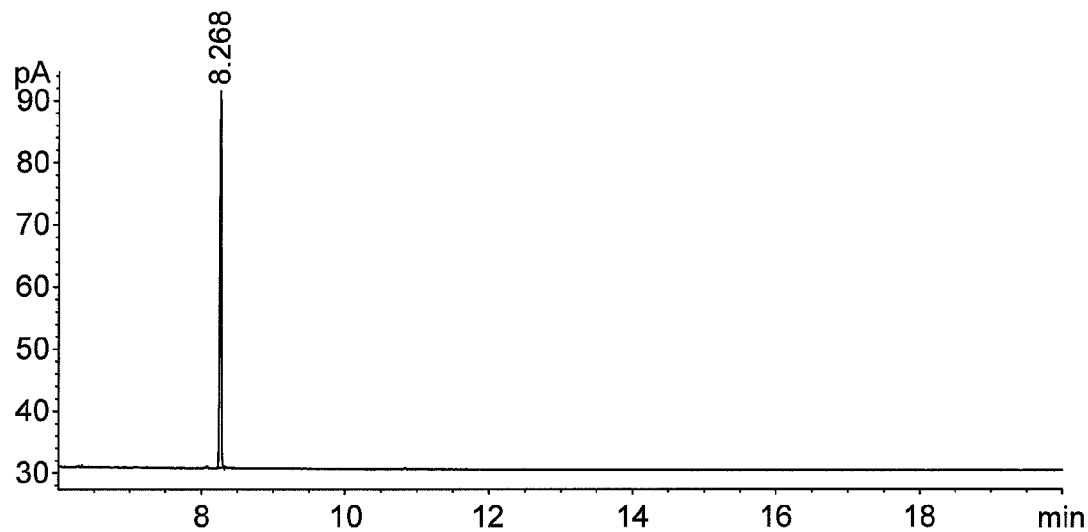
FIGS. 1a-d are GC chromatograms from different chemotype segregants from a 2005.45.13 $F_2$. progeny (Table 2)
 a: is from cannabinoid-free plants;
 b: is from low content and THC predominant plants;
 c: is from high content and THC predominant plants; and
 d: is from high content and CBG predominant plants.
The peaks at 8.2, 16.0 and 16.7 min. represent the internal standard, THC and CBG, respectively.
Figure 1B:
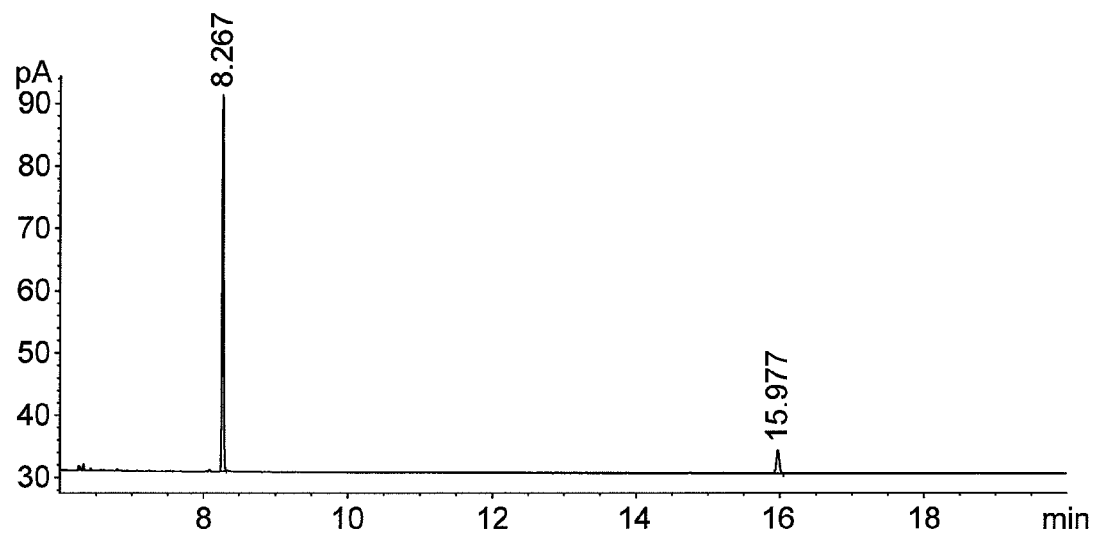
Figure 1C:
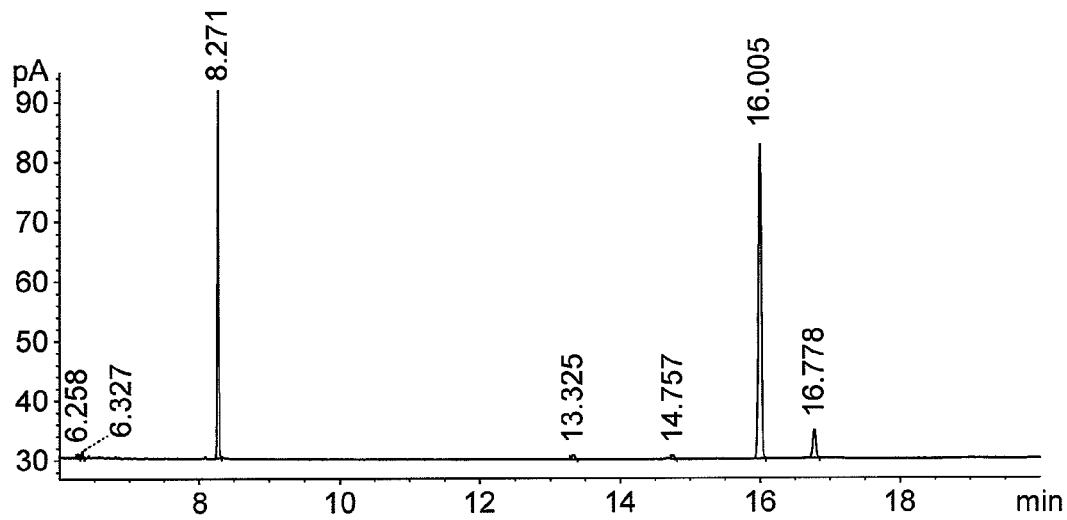
Figure 1D:
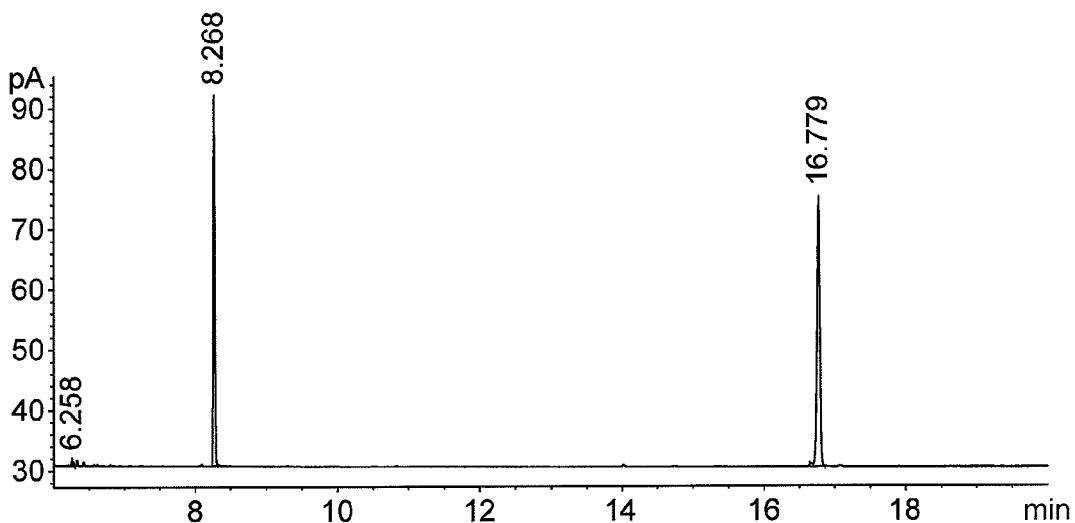

By way of introduction it should be noted that there are many different *Cannabis sativa* varieties and chemotypes. These include both wild type plants and cultivated varieties. The cultivated varieties include plants which have been cultivated as fibre producers (low THC varieties); those that have been bred (illegally) for recreational use (high THC) and more recently medicinal plants which have been selectively bred for their cannabinoid content (one or more cannabinoids predominate) and optionally the profile of e.g. entourage compounds.

In order to produce plants with the desired characteristics it was necessary to "knock out" the expression of cannabinoids in a manner, which did not detrimentally effect the production of e.g. entourage compounds in the medicinal plants. How this was achieved is set out below:

Identification of a Cannabinoid-Free Chemotype Plant.

Because in many countries *cannabis* cultivation is restricted to fibre hemp cultivars having specified "low" levels (typically below either 0.1 or 0.3% w/w of the dry floral tissue) of THC, several breeding programmes have been devoted to meeting these legal limits.

According to a survey of the European commercial fibre cultivars [13], the cultivars bred at the Ukrainian Institute of Fibre Crops (Glukhov, formerly, Federal Research Institute of Bast Crops) have the lowest THC contents and the lowest total cannabinoid contents. The cannabinoid breeding programme at this institute started in 1973. Their usual selective breeding methodology consists of family selection within existing cultivars with a high agronomic value and the elimination, before flowering, of plants with relatively high contents [14] and [15]. This effort has resulted in a gradual decrease of both THC content and total cannabinoid content.

Gorshkova et al. [16] evaluated the densities of sessile and stalked glandular trichomes on the bracteoles of various plants. They found that plants with stalked trichomes had relatively high cannabinoid contents and that their contents were positively correlated with the density of the stalked trichomes. Plants that had solely sessile trichomes always had low contents that were uncorrelated with the densities of the sessile trichomes. Gorshkova et al. [16] also mention plants without glandular trichomes that were found to be cannabinoid-free.

Since then, Ukrainian plant breeders have reported several times on the existence of cannabinoid-free breeding materials [15], [17] and [18]

Pacifico et al. [1,9] analysed individual plants from the Ukrainian cultivar USO 31 and found that one third of the individuals contained no cannabinoids. He also found that a minority of the plants (<10%) in a French fibre cultivar, Epsilon 68, were cannabinoid-free.

The Ukrainian cultivar USO 31 is amongst several varieties of hemp that have been approved for commercial cultivation under subsection 39(1) of the Industrial Hemp Regulations in Canada for the year 2007. At least 2,500 seeds of *Cannabis sativa* USO 31 were deposited with the National Collections of Industrial, Food and Marine Bacteria (NCIMB; Ferguson Building, Craibstone Estate, Bucksburn, Aberdeen, AB21 9 YA, Scotland, U.K.) on Feb. 5, 2015, and have been assigned Accession number: NCIMB 42357.

These cannabinoid free plants are phenotypically and chemotypically different to those developed by the applicant through artificial manipulation and differ from those cannabinoid free plants that have been isolated in nature.

Theoretically, two different physiological conditions could make a plant cannabinoid-free:
(1) a disrupted morphogenesis of glandular trichomes that, according to Sirikantaramas et al. [20], appear to be essential structures for cannabinoid synthesis, and
(2) a blockage of one or more biochemical pathways that are crucial for the formation of precursors upstream of CBG.

The first condition would also seriously affect the synthesis of other secondary metabolites that are produced largely or uniquely in the glandular trichomes.

In 1991, field grown cannabinoid-free plants, resulting from Gorshkova et al. [16] programme were viewed and the bracts and bracteoles of these plants were apparently lacking glandular trichomes. Also, the plants did not exude the characteristic cannabis fragrance. This suggests that the volatile mono- and sesquiterpenes were not produced in these plants. Such cannabinoid free plants might therefore have been considered unsuitable for the purpose of breeding a cannabinoid free plant with typical entourage compounds.

The second condition could also affect metabolites other than cannabinoids, as in the case of an obstruction of the basic pathways of common precursors for different classes of end products.

The IPP incorporated, via GPP, into cannabinoids is derived from the DOX pathway in the plastids [2]. Monoterpenes, diterpenes, carotenoids, phytol and tetraterpenes are also uniquely synthesised in the plastids and one could therefore conclude that the IPP incorporated in these compounds, as with cannabinoids, is derived from the DOX pathway [21].

Sesquiterpenes, sterols and triterpenes are uniquely synthesised in the cytoplasm. Presumably they are synthesised from MVA derived IPP [21] and so do not share a fundamental pathway with the terpenoid moiety of cannabinoids.

Even so, according to Evans [22], there is also evidence for a cooperative involvement of the DOX- and the MVA pathway in the synthesis of certain compounds, through the migration of IPP from the plastids into the cytoplasm and vice versa.

The potentially wider chemical effect of engineering plants with the cannabinoid knockout factor yet which express selected entourage compounds has implications for pharmaceutical cannabis breeding. Cannabinoids, and THC in particular, are generally considered as the major pharmaceutically active components of *Cannabis*. Nevertheless, according to McPartland and Russo [23], the terpenoid fraction may modify or enhance the physiological effects of the entourage compounds (i.e. were broadly speaking comparable to plants grown to produce extracts for pharmaceutical use). In this regard USO-31 had a chemical profile, which was not similar to medicinal varieties in that it was lacking both in cannabinoids, and monoterpenes. Furthermore, the sesquiterpene profile also differed both quantitatively and qualitatively from that of plants used to produce pharmaceutical extracts.

EXAMPLES

Example 1

Breeding Programme

To overcome the problem of creating a reference plant which is, in the case of *Cannabis sativa*, free of cannabinoids BUT which had a chemical profile of entourage compounds resembling pharmaceutical *cannabis*, selective breeding programmes were undertaken.

A first cross was made between the selected cannabinoid free plant USO-31 and a plant having a high cannabinoid content of a given cannabinoid, in this case M35, a high THCV containing plant (83.4% by weight of cannabinoids THCV), and M84, a high CBD containing plant (92.4% by weight of cannabinoids CBD). The high cannabinoid plants were selected both for their high and specific cannabinoid contents and their vigour.

Alternatively, a direct cross with a selected pharmaceutical plant could have been made.

Table 1, bottom 2 rows, provides details of the cannabinoid composition of these parental clones:

TABLE 1

Characteristics of parental clones used in breeding experiments with cannabinoid-free materials.

| Code | Generation/type | Source population | Cannabinoid content[a] | CBDV | CBCV | THCV | CBD | CBC | CBGM[c] | THC | CBG |
|---|---|---|---|---|---|---|---|---|---|---|---|
| M3 | Non-inbred clone | Skunk, marijuana strain | 18 | | | 0.5 | | 1.5 | | 97.2 | 0.8 |
| M16 | Non-inbred clone | Turkish fibre landrace | 12 | | | | 91.5 | 2.6 | 1.3 | 3.8 | 0.8 |
| M35 | S₁ inbred clone | (California Orange × Thai), marijuana strains | 14 | | 1.0 | 83.4 | | | | 15.6 | |
| M84 | F₁ hybrid clone | (Afghan × Skunk) × (Afghan × Haze), hashish and marijuana strains | 15 | 1.0 | | | 92.4 | | 1.0 | 3.7 | 1.9 |

[a]The total cannabinoid content (% w/w) of the floral dry matter assessed at maturity.
[b]The proportions (% w/w) of the individual cannabinoids in the total cannabinoid fraction assessed at maturity.
[c]Cannabigerol-monomethylether.

cannabinoids, providing greater medicinal benefits than the pure cannabinoid compounds alone. As summarized by Williamson and Whalley [24], there are indications that the non-cannabinoid 'entourage' of constituents, such as:

monoterpenes;
sesquiterpenes; and
flavonoids modulate the cannabinoid effects and also have medicinal effects by themselves. Speroni et al. [25] reported an anti-inflammatory effect from an extract that was obtained from a cannabinoid-free chemotype.

Selection

Whilst USO-31 was selected as the source of a "knockout" gene to be introduced into pharmaceutical plants the challenge remained of achieving plants which were devoid of cannabinoids but which retained a good profile of selected Of course other strains containing a high percentage of another cannabinoids e.g. THC, CBDV, CBG, CBGV, CBC, CBCV, CBN and CBNV could be used. By "high" is meant that the specific cannabinoid predominates and would typically comprise greater than 50% by weight of the total cannabinoids present, more particularly greater than 60%, through 70% and 80% to most preferably greater than 90% by weight.

The initial cross generated an F1 progeny (Table 2 rows 1 and 2) which were then self crossed to generate an F2 progeny from which plants having the desired characteristics (zero cannabinoid/good entourage compound chemotype profile) were selected for back crossing to pharmaceutical varieties.

The selected zero-cannabinoid plant, USO-31, was monoecious. i.e. it has unisexual reproductive units (flowers, conifer cones, or functionally equivalent structures) of both sexes appearing on the same plant. In order to self-fertilise USO-31 and mutually cross female plants, a partial masculinisation was chemically induced. Self-fertilisations were performed by isolating plants in paper bags throughout the generative stage. The USO-31 source plants were evaluated for their drug type habit. Inbred seeds from the best individual apparently devoid of cannabinoids and another with only cannabinoid traces were pooled.

i) Crosses of Low/Zero Cannabinoid USO-31 Offspring with M35 and M84

Twenty-four plants of the 2003.8 $F_1$ (table 2, row 2) were evaluated.

TABLE 2

Pedigrees and codes of the progenies studied for chemotype segregation.

| Seed parent[a] | Pollen parent[b] | $F_1$ code | $F_2$ code[c] |
|---|---|---|---|
| M35 (THCV) | USO-31 (low/zero) | 2003.17 | 2003.17.<u>19</u> |
| M84 (CBD) | USO-31 (low/zero) | 2003.8 | 2003.8.<u>21</u> |
| M3 (THC) | 2003.8.21.76 $F_3$ (zero) | 2005.45 | 2005.45.<u>13</u> |
| M16 (CBD) | 2003.8.21.76 $F_3$ (zero) | 2005.46 | 2005.46.<u>27</u> |
| M3 (THC) | 2003.17.19.67 $F_3$ (zero) | 2005.47 | 2005.47.<u>9</u> |
| M16 (CBD) | 2003.17.19.67 $F_3$ (zero) | 2005.48 | 2005.48.<u>7</u> |

[a]Of the parents with cannabinoids present, the major one is indicated in brackets.
[b]The USO-31 pollinators were two plants with very low cannabinoid content and/or true cannabinoid absence. The other pollinators were $F_3$ lines confirmed to be devoid of cannabinoids.
[c]The underlined ciphers in the $F_2$ codes indicate the single $F_1$ individual that was self-fertilised to produce the $F_2$ generation. The majority of the plants had 'normal' cannabinoid contents, falling within a Gaussian distribution range from 1.13 to 4.56%. Three plants had only trace amounts of cannabinoids, ranging from approximately 0.02 up to 0.15%.

Similarly, the 19 plants of the 2003.17 $F_1$ comprised a majority of individuals with a cannabinoid content in the range of from 1.69 to 13.76%, and two plants with cannabinoid traces of only ca. 0.02%.

From both $F_1$s, an individual with only trace cannabinoid amounts was self-fertilised to produce an inbred $F_2$ 2003.8.21 and 2003.17.19. Both $F_2$s comprised plants that were confirmed to be devoid of cannabinoids.

The remaining plants, those with cannabinoids present, could be assigned to two categories on the basis of a discontinuity in the cannabinoid content range:

a group with low contents ranging from trace amounts up to roughly 0.6%; and a group with higher contents.

The newly obtained cannabinoid-free plants designated 2003.8.21 and 2003.17.19 $F_2$ had more branching (typical of a drug type phenotype and in contrast to that of a fibre type phenotype), a stronger fragrance (due to the presence/increase in the terpenes and sesquiterpenes) and higher trichome density (determinable on examination) than the original USO-31 plants.

The cannabinoid-free $F_2$ individuals with the best drug type plant habit, 2003.8.21.76 and 2003.17.19.67, were self-fertilised to produce fixed cannabinoid-free $F_3$ inbred lines (Table 2, rows 3-6, col 2) for use in a backcrossing programme with pharmaceutical production clones M3 (High THC 97.2%) and M16 (High CBD 91.5%) (Table 1, top 2 rows).

Backcrosses were performed in order to obtain cannabinoid-free material, more closely resembling (both qualitatively and quantitatively) the pharmaceutical production clones by way of their non-cannabinoid profile, particularly those of the entourage compounds.

All the Clones Listed in Table 1 were True Breeding for their Chemotype.

ii) Backcrossing of Cannabinoid-Free Lines to Pharmaceutical Production Clones M3 and M16

The cannabinoid-free lines 2003.8.21.76 and 2003.17.19.67, (Table 2, column 2, last 4 rows) were then back crossed with pharmaceutical production clones M3 and M16 and the resulting F1's crossed to generate an F2 progeny.

The resulting progeny had their cannabinoid content evaluated as shown in Table 3 below.

TABLE 3

Total cannabinoid contents of $F_1$ progenies resulting from crosses between two cannabinoid-free inbred lines (P1) and two high content clones (P2).

| | | | Total cannabinoid content (% w/w) | | | |
|---|---|---|---|---|---|---|
| $F_1$ progeny | No. of $F_1$ plants evaluated | $F_1$ individual self-fertilised | P1 | P2 | $F_1$ range Min-avg-max | $F_1$ individual self-fertilised |
| 2005.45 | 57 | 2005.45.13 | 0 | 18 | 0.22-0.58-1.09 | 0.89 |
| 2005.46 | 57 | 2005.46.27 | 0 | 12 | 0.16-0.46-1.00 | 0.47 |
| 2005.47 | 57 | 2005.47.9 | 0 | 18 | 0.24-0.45-0.75 | 0.36 |
| 2005.48 | 57 | 2005.48.7 | 0 | 12 | 0.10-0.42-1.25 | 0.83 |

Within the $F_1$s the cannabinoid contents showed a single Gaussian distribution. The $F_1$ contents were much lower than the parental means and therefore much closer to the cannabinoid-free parent than to the production parent. The $F_1$s were well covered with trichomes and were quite fragrant.

In respect of the cannabinoid composition, the 2005.45 $F_1$ segregated into two chemotypes: THC predominant plants and mixed CBD/THC plants, in a 1:1 ratio.

The 2005.46 $F_1$ had a uniform CBD chemotype.

The 2005.47 $F_1$ was uniform and consisted of THC plants, all with a minor proportion of THCV.

The 2005.48 $F_1$ was uniform and consisted of CBD/THC plants that also had minor proportions of CBDV and THCV.

Per $F_1$, one individual was selected on the basis of criteria such as 'drug type morphology' (e.g. branching) and minimal monoeciousness to produce back cross generations. These individuals were used for a repeated pollination of M3 or M16, which is not discussed here.

To examine chemotype segregation, the selected $F_1$ individuals were also self-fertilised to produce large inbred $F_2$s.

FIG. 1 shows chromatograms of different chemotype segregants from the 2005.45.13 $F_2$. FIG. 1a is the chromatogram for a zero cannabinoid plant.

Figure 2A:
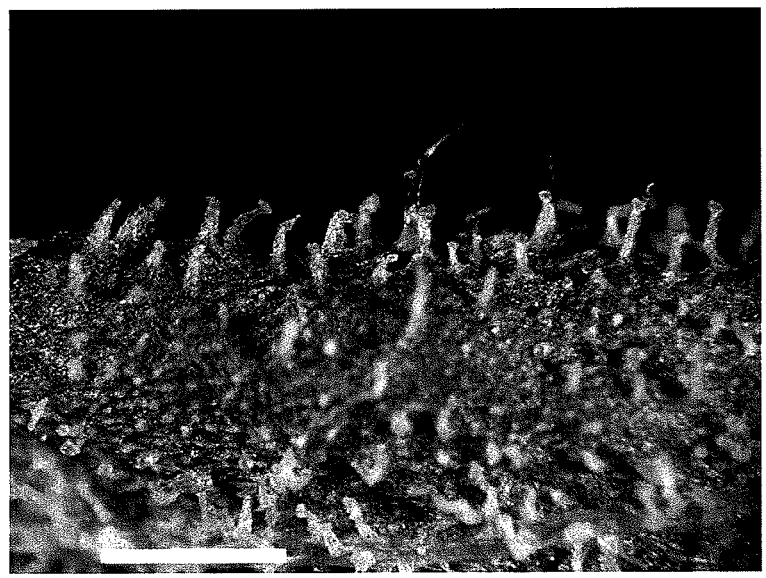
FIG. 2a-d are microscopic images of the bracteole surfaces from different chemotype segregants from the 2005.45.13 $F_2$ progeny.
 a: is from cannabinoid-free plants;
 b: is from low content and THC predominant plants;
 c: is from high content and THC predominant plants; and
 d: is from high content and CBG predominant plants.
(The bar represents 500 μm)

The different chemotype segregants were microscopically compared. The cannabinoid-free plants of each progeny all had small, grey, dull trichomes of various shapes (FIG. 2a). Some were headless; some were pinhead and shrivelled, either flat, convex or concave.

Figure 2B:
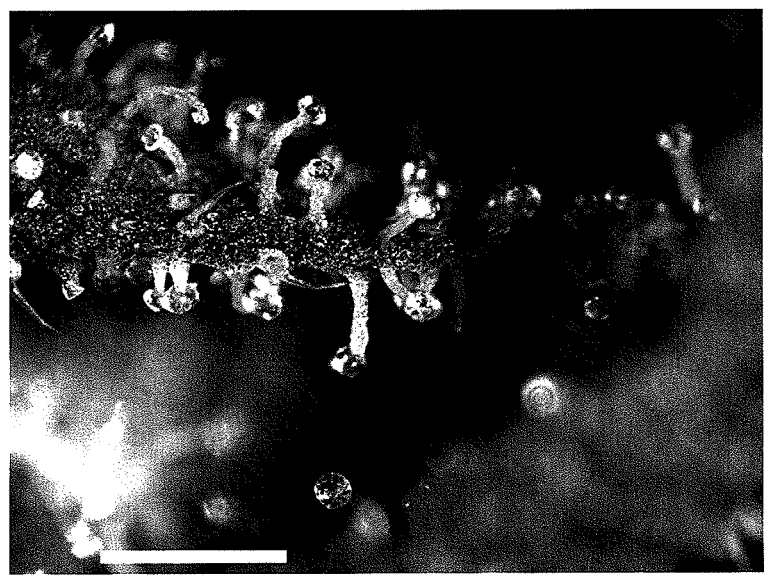
Figure 2C:
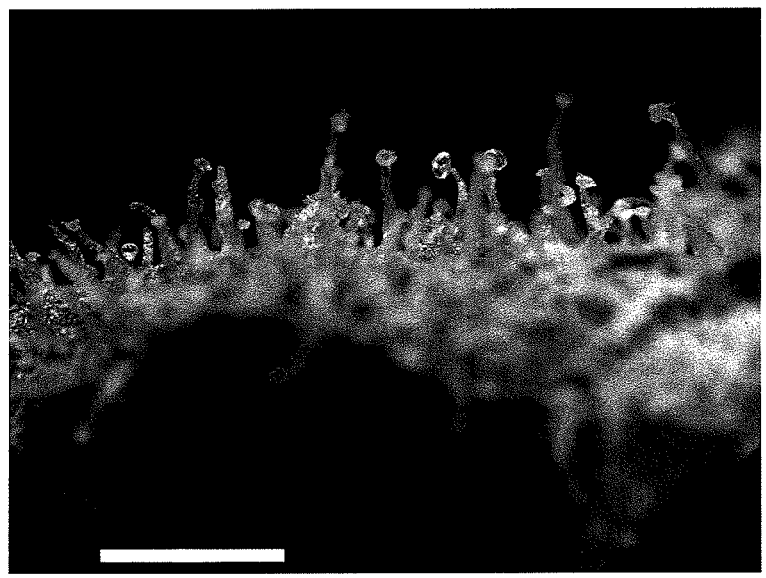
Figure 2D:
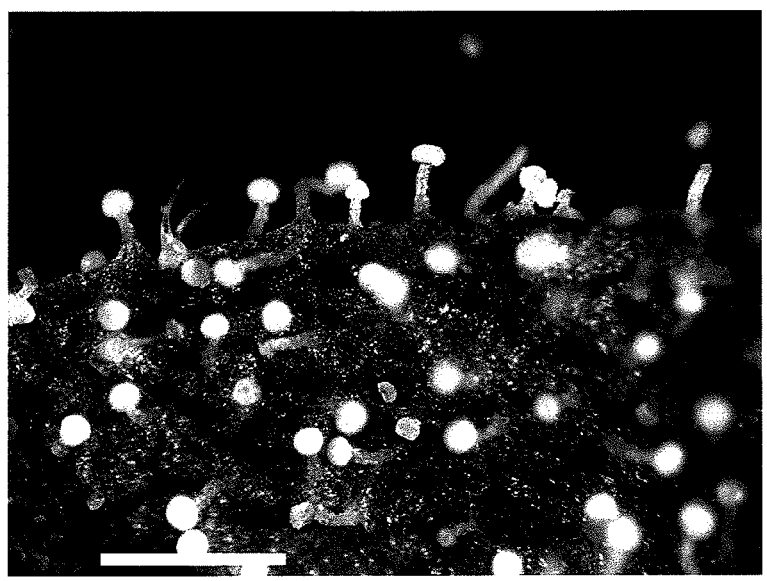

By way of contrast:

The high content CBD- and/or THC-predominant individuals of each group all had big, round clear heads that sparkled under the lamp (FIG. 2b);

The low content plants from each progeny were almost indistinguishable from the cannabinoid-free plants except that there was an occasional small but bright trichome in some (FIG. 2c); and The high content CBG predominant plants from the 2005.45.13 $F_2$ had big, round, opaque white heads (FIG. 2d), clearly distinct from the transparent ones occurring on the THC predominant plants of the same progeny.

The low content CBG predominant 2005.45.13 plants did not show opaque white trichome heads and were indistinguishable from the low content THC predominant plants. Neither were white trichome heads observed in any of the cannabinoid-free plants of this progeny.

As an indication of their vigour, the total above ground dry weights of all the cannabinoid-free- and the high content segregants were assessed. Per progeny, per segregant group the weights showed a Gaussian distribution.

For the 2005.45.13, 2005.46.27 and the 2005.47.9 progenies the cannabinoid-free individuals on average had a ca. 10% higher dry weight than the high content individuals.

In the 2005.48.7 progeny however, the average weight of the high content group exceeded that of the cannabinoid-free group by about 10%.

In order to characterize the plants a chemical analysis of both the cannabinoid content, and selected other chemicals, was undertaken as set out below:

Example 2 i) Analysis of Cannabinoid Content and Other Chemicals

Mature floral clusters were sampled from every individual plant considered in the breeding experiments. Sample extraction and GC analysis took place as described by de Meijer et al. [26].

The identities of the detected compounds were confirmed by GC-MS. Cannabinoid peak areas were converted into dry weight concentrations using a linear calibration equation obtained with a CBD standard range. The contents of the individual cannabinoids were expressed as weight percentages of the dry sample tissue. The total cannabinoid content was calculated and the weight proportions of the individual cannabinoids in the cannabinoid fraction were used to characterize the cannabinoid composition.

ii) Chemical Comparison of Bulk Segregants

Each of the six $F_2$s listed in Table 2 segregated into:
cannabinoid-free plants;
plants with cannabinoid traces; and
plants with high cannabinoid contents.

In each case, per $F_2$, the floral leaves, bracts and bracteoles of all the cannabinoid-free plants were pooled and homogenised, as was the floral fraction of all the plants belonging to the group with high cannabinoid contents. The different bulks from the:

2005.45.13 (from M3-THC),
2005.46.27 (from M16-CBD),
2005.47.9 (from M3-THC) and
2005.48.7 (from M16-CBD) $F_2$ were steam-distilled and the essential oil yields were assessed.

The monoterpene and sesquiterpene composition of these essential oils was analysed by Gas Chromatography with Flame Ionisation Detection (GC-FID).

The relative amounts of a wide range of entourage compounds in the bulk homogenates of:

2003.8.21 (from M84-CBD) and
2003.17.19 (from M35 THCV) $F_2$s were also compared by using the following analytical techniques:

a) Gas Chromatography—Mass Spectrometry (GC-MS)

To obtain comparative fingerprints, GC-MS analyses were performed on a HP5890 gas chromatograph, coupled to a VG Trio mass spectrometer. The GC was fitted with a Zebron fused silica capillary column (30 m×0.32 mm inner diameter) coated with ZB-5 at a film thickness of 0.25 µm (Phenomenex). The oven temperature was programmed from 70° C. to 305° C. at a rate of 5° C./min. Helium was used as the carrier gas at a pressure of 55 kPa. The injection split ratio was 5:1.

b) Gas Chromatography with Flame Ionisation Detection (GC-FID)

GC profiles of terpenoids were generated in the splitless mode with a HP5890 gas chromatograph. The GC was fitted with a Zebron fused silica capillary column (30 m×0.32 mm inner diameter) coated with ZB-624 at a film thickness of 0.25 µm (Phenomenex). The oven temperature was held at 40° C. for 5 minutes, programmed to 250° C. at a rate of 10° C./min then held at 250° C. for 40 minutes. Helium was used as the carrier gas at a pressure of 9.2 psi. The injection split ratio was 10:1.

c) High-Performance Liquid Chromatography (HPLC) with Ultra-Violet (UV) Detection HPLC profiles were obtained using methods specific to a variety of compound classes. All samples were analysed using Agilent 1100 series HPLC systems (i) Cannabinoid profiles were generated using a $C_{18}$ (150×4.6 mm, 5 µm) analytical column. The mobile phase consisted of acetonitrile, 0.25% w/v acetic acid and methanol at a flow rate of 1.0 ml/min and UV profiles were recorded at 220 nm.

(ii) Carotenoid profiles were generated using a Varian Polaris $C_{18}$ (250×4.6 mm, 5 µm) analytical column. The mobile phase consisted of acetonitrile:methanol:dichloromethane:water at a flow rate of 1.2 ml/min and UV profiles were recorded at 453 nm.

(iii) Chlorophyll profiles were generated using the same column, mobile phase and flow rate described for carotenoids. UV profiles were recorded at 660 nm.

(iv) Non-polar compound profiles (triglycerides, sterols etc) were generated by a gradient LC method using a Phenomenex Luna $C_{18}$ (2) (150×2.0 mm, 5 µm) analytical column. The mobile phase consisted of solvent A (acetonitrile:Methyl-tert-butyl-ether (9:1)) and solvent B (water) with the proportion of B decreased linearly from 13% to 0% over 30 minutes then held constant for 20 minutes at a flow rate of 1.0 ml/min. The flow rate was then increased linearly to 1.5 ml/min over 40 minutes and UV profiles were recorded at 215 nm.

(v) Polar compound profiles (phenolics) were generated by a gradient LC method using an Ace $C_{18}$ (150×4.6 mm, 5 µm) analytical column. The mobile phase consisted of solvent A (acetonitrile:methanol, 95:5) and solvent B (0.25% w/v acetic acid:methanol, 95:5). The proportion of B was decreased linearly from 75% to 15% over 30 minutes then held constant for 10 minutes at a flow rate of 1.0 ml/min and UV profiles were recorded at 285 nm.

Results

Chemical Comparison of Cannabinoid-Free- and High Content Bulks

The yields and compositions of steam-distilled essential oils from bulked cannabinoid-free- and bulked high content segregants of the four $F_2$ progenies are presented in Table 4 below.

| A R/T | B | C Parent USO-31 Zero cannabinoid Control 1 | D Parent M35 83.4% THCV | E Parent M84 92.4% CBD | F Intermediate USO-31 × M35 F2 Table 5 | G Intermediate USO-31 × M84 F2 Table 5 | H Back cross parent M16 91.5% CBD Control 2 | I Back cross parent M3 97.2% THC Control 3 |
|---|---|---|---|---|---|---|---|---|
| | Weight of material (g) | 73.8 g | | | | | 117.7 g | 120.5 g |
| | Volume of oil (ml) | 0.10 ml | | | | | 0.3 | 0.95 |
| | % OIL (% v/w) | 0.14% | | | | | 0.25 | 0.79 |
| | MONOTERPENES | | | | | | | |
| 10.3 | alpha-pinene | UDL | | | | | 7.3 | 4.95 |
| 11.8 | beta-pinene | UDL | | | | | 2.65 | 3.58 |
| 12.2 | myrcene | UDL | | | | | 42.55 | 39.02 |
| 13.7 | limonene | UDL | | | | | 5.27 | 6.66 |
| 14.2 | beta-ocimene | UDL | | | | | 2.5 | UDL |
| 16 | Linalol | UDL | | | | | 3.68 | 4.65 |
| 17.8 | cis-verbenol | UDL | | | | | UDL | UDL |
| 18 | trans-verbenol | | | | | | UDL | UDL |
| TOTAL | | 0 | | | | | 63.95 | 58.86 |
| | SESQUITERPENES | | | | | | | |
| 28.8 | caryophyllene trans alpha | 33.02 | | | | | 25.11 | 16.44 |
| 28.9 | bergamotene | 5.75 | | | | | UDL | 2.45 |
| 29.2 | (z)-beta farnesene | 9.34 | | | | | UDL | 4.25 |
| 29.8 | humulene | 11.96 | | | | | 8.71 | 7.65 |
| 30.7 | Unidentified | 5.95 | | | | | | |
| 30.8 | (e)-beta farnesene | 1.59 | | | | | 2.23 | UDL |
| 31.1 | gamma gurjunene | 4.01 | | | | | UDL | UDL |
| 31.3 | delta guaiene | | | | | | UDL | UDL |
| 31.6 | Unidentified | 1.03 | | | | | | |
| 32.3 | (e)-nerolidol | 0.98 | | | | | UDL | 5.31 |
| 32.7 | unknown | | | | | | UDL | 5.03 |
| 33.6 | Unidentified | 1.91 | | | | | | |
| 33.8 | caryophyllene oxide | 6.42 | | | | | UDL | UDL |
| 34.5 | humulene epoxide II | 3.17 | | | | | UDL | UDL |
| 36.4 | alpha bisabolol | | | | | | UDL | UDL |
| 47.5 | Unidentified | 7.48 | | | | | | |
| TOTAL | | 92.61 | | | | | 36.05 | 41.13 |

| A R/T | B | J Final zero 2005.45.13 M3 backcross zero | K 2005.45.13 high | L Final zero 2005.46.27 M16 backcross zero | M 2005.46.27 high | N Final zero 2005.47.9 M3 backcross zero | O 2005.47.9 high | P Final zero 2005.48.7 M16 backcross zero | Q 2005.48.7 high |
|---|---|---|---|---|---|---|---|---|---|
| | Weight of material (g) | 104.5 g | 88.1 g | 95.1 | 92.2 | 87.1 | 86.4 | 85.2 | 123.6 |
| | Volume of oil (ml) | 0.68 | 0.5 | 0.64 | 0.8 | 0.24 | 0.74 | 0.35 | 0.78 |
| | % OIL (% v/w) | 0.65 | 0.57 | 0.67 | 0.87 | 0.28 | 0.87 | 0.41 | 0.63 |
| | MONOTERPENES | | | | | | | | |
| 10.3 | alpha-pinene | 16.64 | 11.83 | 28.53 | 26.8 | 10.27 | 2.86 | 33.52 | 22.53 |
| 11.8 | beta-pinene | 7.65 | 6.58 | 12.6 | 9.37 | 5.57 | 2.22 | 15.51 | 8.98 |
| 12.2 | myrcene | 51.1 | 42.11 | 34.16 | 42.86 | 19.84 | 41.45 | 24.82 | 36.47 |
| 13.7 | limonene | 4.76 | 4.53 | 6.41 | 7.41 | 7.27 | 5.54 | 5.17 | 4.58 |
| 14.2 | beta-ocimene | UDL | UDL | UDL | UDL | UDL | 9.58 | UDL | 8.6 |
| 16 | Linalol | 1.62 | 2.78 | UDL | UDL | 10.48 | 2.95 | 2.91 | UDL |
| 17.8 | cis-verbenol | UDL | UDL | UDL | UDL | UDL | UDL | 1.73 | UDL |
| 18 | trans-verbenol | UDL | UDL | UDL | UDL | 3.31 | UDL | 2.61 | UDL |
| TOTAL | | 81.77 | 67.83 | 81.7 | 86.44 | 56.74 | 64.6 | 86.27 | 81.16 |
| | SESQUITERPENES | | | | | | | | |
| 28.8 | caryophyllene trans alpha | 3.9 | 12.25 | 7.28 | 8.35 | 7.97 | 15.93 | 4.73 | 9.84 |
| 28.9 | bergamotene | 3.86 | 3.71 | 1.71 | UDL | UDL | UDL | UDL | UDL |
| 29.2 | (z)-beta farnesene | 4.83 | 6.05 | 2.78 | 1.95 | UDL | 3.48 | UDL | 1.86 |
| 29.8 | humulene | 3.04 | 6.83 | 3.27 | 3.26 | 7.88 | 7.68 | 2.12 | 3.69 |
| 30.8 | (e)-beta farnesene | UDL | 1.69 | UDL | UDL | UDL | UDL | UDL | UDL |
| 31.1 | gamma gurjunene | UDL | UDL | UDL | UDL | UDL | 1.78 | UDL | UDL |
| 31.3 | delta guaiene | UDL | UDL | UDL | UDL | 3.64 | 4.67 | 1.67 | 3.44 |
| 32.3 | (e)-nerolidol | UDL | 1.65 | UDL | UDL | UDL | UDL | UDL | UDL |
| 32.7 | unknown | UDL | UDL | UDL | UDL | UDL | 1.86 | UDL | UDL |

-continued

| | | | | | | | | |
|---|---|---|---|---|---|---|---|---|
| 33.8 | caryophyllene oxide | 2.62 | UDL | 3.25 | UDL | 13.43 | UDL | 5.19 | UDL |
| 34.5 | humulene epoxide II | UDL | UDL | UDL | UDL | 6.06 | UDL | UDL | UDL |
| 36.4 | alpha bisabolol | UDL | UDL | UDL | UDL | 4.27 | UDL | UDL | UDL |
| TOTAL | | 18.25 | 32.18 | 18.29 | 13.56 | 43.25 | 35.4 | 13.71 | 18.83 |

In three (2005.46.27, 2005.47.9, and 2005.48.7), the cannabinoid-free bulks contained less essential oil than the high content ones.

In 2005.45.13 however, the cannabinoid-free bulk was slightly richer.

No significant qualitative differences in the essential oil composition were found, only minor quantitative ones, which generally did not show a systematic pattern.

The only consistent quantitative difference between the low and high content progeny was difference was found for caryophyllene oxide that in all four progenies, reached a higher proportion in the cannabinoid-free bulks than in the high content bulks.

When the zero cannabinoid backcross plants of the invention were compared to control 1 (the original zero cannabinoid plant which was also devoid of monoterpenes) and controls 2 and 3 (the pharmaceutical plants with a high cannabinoid content and a range of entourage compounds) the following differences were observed:
1. The volume of oil (%) obtained by steam distillation in the zero cannabinoid plants of the invention was on average 0.50%. By way of comparison control 1 is 0.14%, and the mean of control 2 and 3 was 0.52%. In other words the % oil is representative of the pharmaceutical clones.
2. The total measured monoterpene fraction in the zero cannabinoid plants of the invention was on average about 76. By way of comparison control 1 is 0, and the mean of control 2 and 3 was about 61. In other words the monoterpene fraction is representative of the pharmaceutical clones.
3. Within the monoterpence fraction in the zero cannabinoid plants of the invention the predominant terpene was myrcene, followed by alpha pinine and beta pinine with smaller amounts of limonine and linalol. Whilst quantitatively there were differences compared to the pharmaceutical controls there was, broadly speaking, a qualitative relationship.
4. The total measured sesquiterpene fraction in the zero cannabinoid plants of the invention was on average about 23. By way of comparison, control 1 is about 93, and the mean of controls 2 and 3 was about 39. In other words the sesquiterpene fraction is much more representative of the pharmaceutical clones than control 1.
5. Within the sesquiterpene fraction in the zero cannabinoid plants of the invention the predominant sesquiterpene were carophyllene, humulene and carophyllene oxide (accounting for more than 50% of the sesquiterpene fraction). Whilst there were differences compared to the pharmaceutical controls (where quantitatively carophyllene and humulene were again the most significant sesquiterpenes but carophyllene oxide was absent) there was, broadly speaking a qualitative, if not quantitative relationship between the plants of the invention and the pharmaceutical plants as compared to the starting zero cannabinoid plants which had much higher levels of sesquiterpenes and a wider detectable range of sesquiterpenes.

By way of comparison Table 5 gives some analytical data on the intermediate plants generated. It is a comparison of the different segregant bulks from 2003.8.21 and 2003.17.19 for a variety of compound classes.

TABLE 5

The composition of bulked cannabinoid-free-(Zero) and bulked high content segregants of two intermediate $F_2$ progenies.

| $F_2$ progenies | 2003.8.21 | | 2003.17.19 | |
|---|---|---|---|---|
| Segregant bulks | Zero | High | Zero | High |
| (i) Cannabinoids[c] | | | | |
| CBDV | — | 0.00566 | — | — |
| THCV | — | — | — | 0.08814 |
| CBGV | — | — | — | 0.01157 |
| CBD | — | 0.47868 | — | — |
| CBC | — | 0.04855 | — | 0.02771 |
| CBGM | — | 0.00671 | — | — |
| THC | — | 0.01605 | — | 0.32459 |
| CBG | — | 0.20785 | — | 0.05573 |
| CBN | — | — | — | 0.01179 |
| Triterpenes[b] | | | | |
| Squalene | $4.1 \times 10^7$ | $7.9 \times 10^7$ | $2.1 \times 10^7$ | $1.9 \times 10^7$ |
| Unidentified hydrocarbon | $5.2 \times 10^8$ | $5.4 \times 10^8$ | $1.1 \times 10^8$ | $1.6 \times 10^8$ |
| Unidentified alcohol 1 | $3.8 \times 10^8$ | $5.1 \times 10^8$ | $1.1 \times 10^8$ | $3.3 \times 10^8$ |
| Unidentified alcohol 2 | $1.3 \times 10^8$ | $1.3 \times 10^8$ | $5.5 \times 10^7$ | $1.4 \times 10^8$ |
| Diterpenes[c] | | | | |
| Phytol | 0.0587 | 0.0591 | 0.0511 | 0.0487 |
| Sesquiterpenes[c] | | | | |
| Beta-caryophyllene | 0.0043 | 0.0105 | 0.0022 | 0.0102 |
| Alpha-caryophyllene | 0.0022 | 0.0037 | 0.0027 | 0.0035 |
| Caryophyllene oxide | 0.0049 | 0.0041 | 0.0020 | 0.0041 |
| Nerolidol | 0.0030 | 0.0024 | 0.0043 | 0.0027 |
| Monoterpenes[c] | | | | |
| Alpha-pinene | 0.0010 | 0.0015 | 0.0015 | 0.0085 |
| Myrcene | 0.0017 | 0.0057 | 0.0024 | 0.0180 |
| Limonene | — | 0.0011 | — | 0.0015 |
| Linalol | 0.0030 | 0.0053 | 0.0035 | 0.0053 |
| Long-chain alkanes[b] | | | | |
| Nonacosane | $1.1 \times 10^9$ | $9.5 \times 10^8$ | $2.0 \times 10^8$ | $4.7 \times 10^8$ |
| Heptacosane | $1.5 \times 10^8$ | $1.8 \times 10^8$ | $5.5 \times 10^7$ | $4.7 \times 10^7$ |
| Pentacosane | $2.5 \times 10^7$ | $2.0 \times 10^7$ | $1.3 \times 10^7$ | $7.4 \times 10^6$ |
| Hentriacontane | $2.7 \times 10^8$ | $1.6 \times 10^8$ | $4.2 \times 10^7$ | $7.3 \times 10^7$ |
| Sterols[b] | | | | |
| Sitosterol | $2.3 \times 10^8$ | $1.5 \times 10^8$ | $7.6 \times 10^7$ | $2.9 \times 10^8$ |
| Campesterol | $6.6 \times 10^7$ | $4.0 \times 10^7$ | $1.3 \times 10^7$ | $5.9 \times 10^7$ |
| Stigmasterol | $5.1 \times 10^7$ | $3.3 \times 10^7$ | $8.1 \times 10^6$ | $4.6 \times 10^7$ |
| Fatty acids[a] | | | | |
| Palmitic acid | ✓ | ✓ | ✓ | ✓ |
| Linoleic acid | ✓ | ✓ | ✓ | ✓ |
| Oleic acid | ✓ | ✓ | ✓ | ✓ |

TABLE 5-continued

The composition of bulked cannabinoid-free-(Zero) and bulked high content segregants of two intermediate $F_2$ progenies.

| $F_2$ progenies | 2003.8.21 | | 2003.17.19 | |
|---|---|---|---|---|
| Segregant bulks | Zero | High | Zero | High |
| Stearic acid | ✓ | ✓ | ✓ | ✓ |
| Linolenic acid | ✓ | ✓ | ✓ | ✓ |
| Aldehydes[b] | | | | |
| Octadecanal | $2.4 \times 10^7$ | $5.5 \times 10^7$ | $8.1 \times 10^7$ | $6.9 \times 10^7$ |
| Vitamins[b] | | | | |
| Vitamin E | $1.6 \times 10^7$ | $2.1 \times 10^7$ | $1.2 \times 10^7$ | $1.3 \times 10^7$ |
| (ii) Carotenoids[a] | | | | |
| Beta-carotene | ✓ | ✓ | ✓ | ✓ |
| (iii) Chlorophylls[a] | | | | |
| Chlorophyll a | ✓ | ✓ | ✓ | ✓ |
| Triglycerides[d] | | | | |
| GGL | 49.13 | 22.67 | 39.07 | 32.81 |
| GLL | 19.40 | 7.00 | 9.71 | 7.03 |
| OLLn | 39.37 | 22.87 | 48.23 | 39.36 |
| OLL | 20.14 | 6.21 | 15.53 | 10.80 |

[a]compounds scored as present (✓) or absent (—).
[b]quantities expressed as GC-MS peak areas.
[c]quantities expressed as w/w contents.
[d]quantities expressed as HPLC-UV peak areas.

In general the differences between the entourages of the cannabinoid-free and the high content bulks were only quantitative. Limonene was an exception, as it was not detected in the cannabinoid-free bulks whereas a minor presence was found in both of the high content bulks.

However, the essential oil data in Table 4 does not confirm this finding for the other $F_2$s. Likewise, Table 5 does not show the difference in caryophyllene oxide as it appears in Table 4.

Both progenies in Table 5 had consistently higher levels of four different triglycerides in the cannabinoid-free bulks than the high content bulks. The occurrence of none of the entourage compounds listed in the Tables 4 and 5 appears to be critically associated with the presence or absence of cannabinoids.

With the reported exception of the triglycerides, the quantitative differences in the entourage compounds does not show a consistent trend between cannabinoid-free- and high content bulks.

Figure 3A:
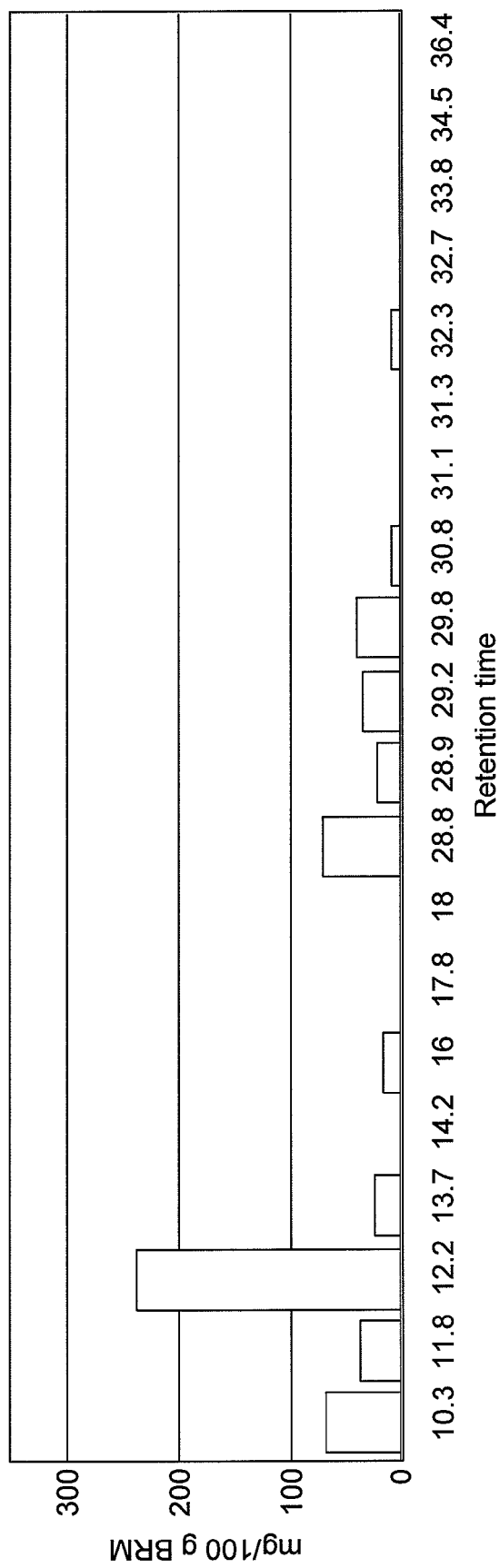
FIG. 3 shows graphically, the chemical profile (both qualitatively and quantitatively) of respectively:
 Top—a high cannabinoid bulk segregant;
 Middle—a cannabinoid free bulk segregant of the invention; and
 Bottom—a pharmaceutical production comparator (M3).
Figure 3B:
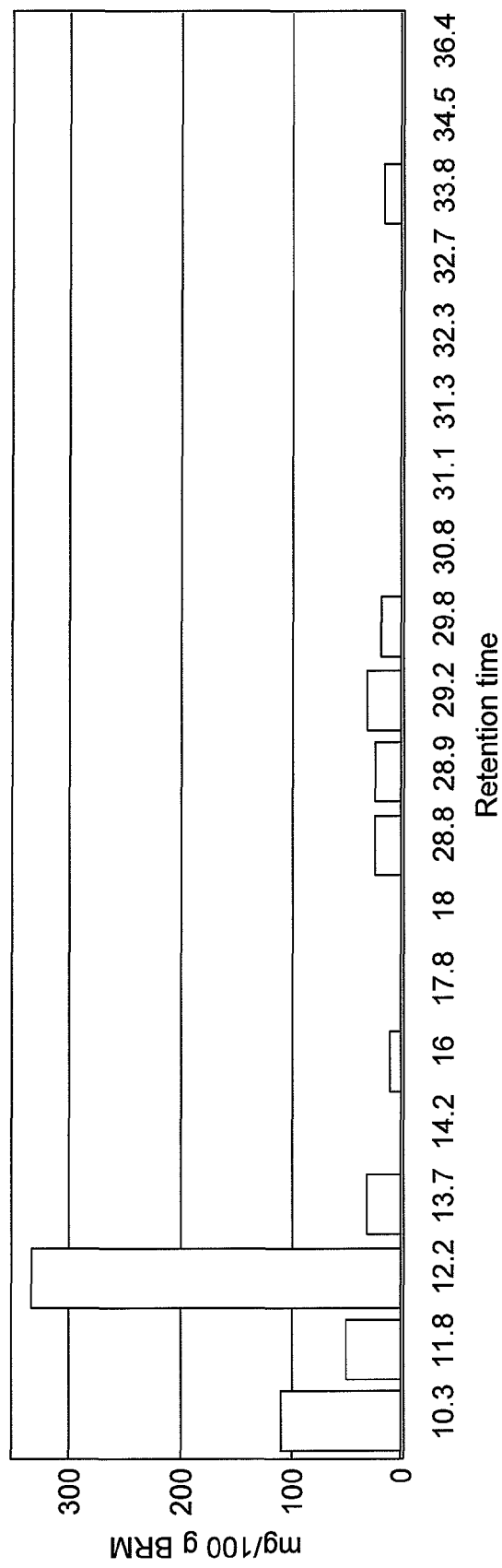
Figure 3C:
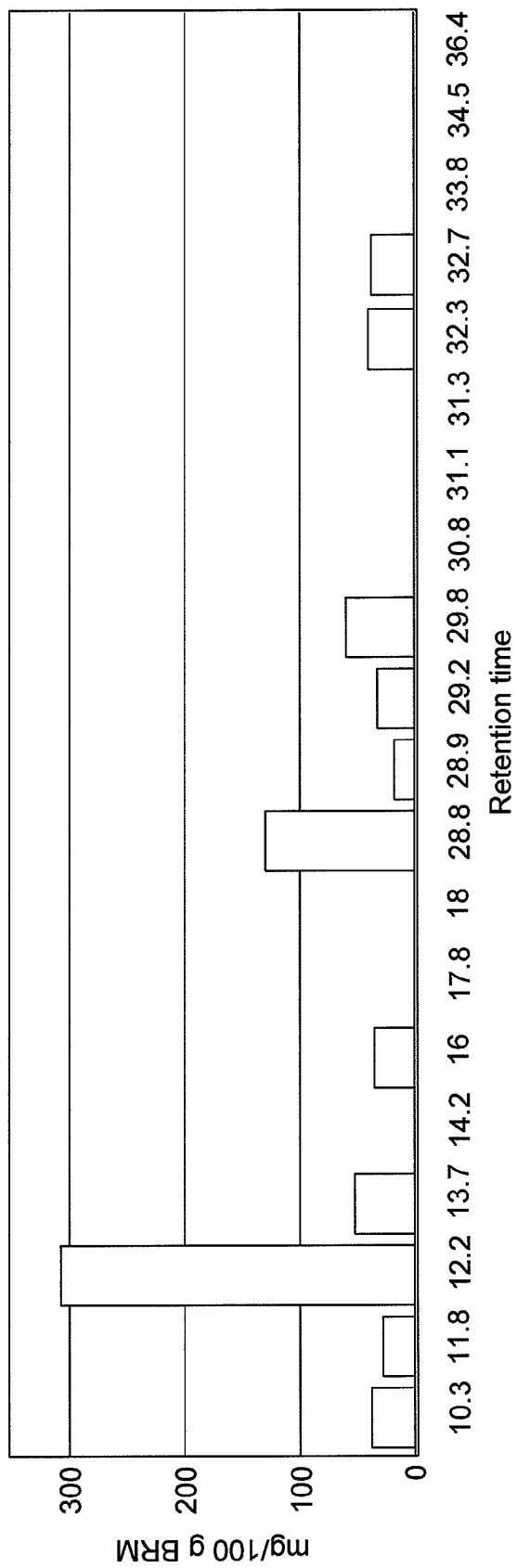

This is most clearly seen in FIG. 3, which compares high cannabinoid bulks with cannabinoid free bulks. It also shows an M3 pharmaceutical bulk. What is apparent from a comparison of these extracts is that the profiles between the high content bulk and the cannabinoid free bulk of the segregating plants are very similar and that further more there is substantial similarity to the pharmaceutical extract M3, particularly at the earlier retention times (less than 30 minutes).

Discussion

The cannabinoid-free segregants resulting from backcrosses with high content drug clones had glandular trichomes in normal densities but the trichome heads were dull and much smaller than those of high cannabinoid content sister plants. Nevertheless the trichomes of cannabinoid-free segregants appear to be functional metabolic organs, as the chemical comparison of contrasting segregant bulks did not reveal big differences in the content and composition of volatile terpenes, which are also produced in the trichomes. The absence of cannabinoids probably causes the small trichome heads, rather than being a result of them.

The abundant presence of apparently functional trichomes on the cannabinoid-free plants rules out that the absence of cannabinoids is due to a disrupted morphogenesis of the glandular trichomes. It thus appears that the cannabinoid knockout factor is not derived from the gland free plants selected by Gorshkova et al [16].

It is more plausible that the absence of cannabinoids is attributable to the blockage of one or more biochemical pathways that are crucial for the formation of precursors upstream of CBG. As the chemical entourage of cannabinoid-free plants is intact, the obstacle is probably not in the MVA and DOX pathways towards IPP.

A blocked MVA pathway would not affect cannabinoid synthesis [2], but it should reduce levels of sesquiterpenes, sterols and triterpenes [21].

A blockage of the DOX pathway would obstruct the synthesis of the terpenoid moiety of cannabinoids [2] but it should also negatively affect the synthesis of monoterpenes, diterpenes, carotenoids, phytol and tetraterpenes [21].

An alternative is that the knockout allele encodes a defective form of the enzyme GOT [1] that catalyses the condensation of resorcinolic acids (OA and DA) with GPP into CBG. However, with such a mechanism one would expect an accumulation of the phenolic moieties OA and/or DA in the cannabinoid-free segregants. Our GC method for cannabinoid analysis detects the decarboxylated forms of both acids but they were observed in none of the cannabinoid-free plants' chromatograms.

The most plausible hypothesis for the absence of cannabinoids appears to be a blockage in the polyketide pathway towards the phenolic moieties OA and DA. Whatever the working mechanism of the cannabinoid knockout factor is, one would expect that a functional synthase dominates a non-functional version, and so it remains obscure as to why the heterozygous genotypes (O/o) have such a strongly suppressed cannabinoid synthesis.

The essential oil comparison and the chromatographic fingerprinting of contrasting segregant bulks demonstrated that except the cannabinoids, all the monitored compound classes were present in both segregant groups. The relative levels of the compound classes did vary between the contrasting segregant groups but not usually in a systematic way.

The quantitative differences between contrasting bulks could be attributable to the fact that in cannabinoid-free plants the trichome heads, as the metabolic centres for a range of end products, are not inflated with cannabinoids. This may change the physical environment in which the reactions occur so that it quantitatively affects the synthesis of entourage compounds. The fact that large amounts of basic cannabinoid precursors are not incorporated may also affect equilibriums of other biosynthetic reactions.

A further benefit of the plants of the present invention is that they can be used to create plant extracts containing cannabinoids in quantities/purities, which could not be achieved naturally. Such plant extracts providing the benefits arising from the presence of one or more selected entourage compounds. The cannabinoids, which could be introduced to the cannabinoid free extracts, could include one or more natural cannabinoids, synthetic cannabinoids or biosynthetic cannabinoids (modified natural cannabinoids). This would produce a "designer" plant extract that could be used in clinical trials or as medicines.

The benefits of natural or biosynthetic cannabinoids over synthetic cannabinoids lies in the fact that all of the cannabinoids are in the active form as opposed to a racemic mixture.

Other aspects of the invention will be clear to the skilled artisan and need not be repeated here. Each reference cited herein is incorporated by reference in its entirety for the relevant teaching contained therein.

The terms and expressions that have been employed are used as terms of description and not of limitation, and there is no intention in the use of such terms and expressions of excluding any equivalents of the features shown and described or portions thereof, it being recognized that various modifications are possible within the scope of the invention.

REFERENCES

[1] Fellermeier M, Zenk M H (1998) Prenylation of olivetolate by a hemp transferase yields cannabigerolic acid, the precursor of tetrahydrocannabinol. FEBS Letters 427:283-285

[2] Fellermeier M, Eisenreich W. Bacher A, Zenk M H (2001) Biosynthesis of cannabinoids, incorporation experiments with $^{13}$C-labeled glucoses. Eur. J. Biochem. 268:1596-1604

[3] Rahaijo T J, Chang W T, Verberne M C, Peltenburg-Looman A M G, Linthorst H J M, Verpoorte R (2004a) Cloning and over-expression of a cDNA encoding a polyketide synthase from Cannabis sativa. Plant Physiology and Biochemistry 42:291-297

[4] Taura F, Morimoto S, Shoyama Y, Mechoulam R (1995) First direct evidence for the mechanism of delta-1-tetrahydrocannabinolic acid biosynthesis. J Am Chem Soc 38:9766-9767

[5] Taura F, Morimoto S, Shoyama Y (1996) Purification and characterization of cannabidiolic-acid synthase from Cannabis sativa L. J of Biol Chem 271:17411-17416

[6] Gaoni Y, Mechoulam R (1966) Cannabichromene, a new active principle in hashish. Chemical Communications 1:20-21

[7] Morimoto S, Komatsu K, Taura F, Shoyama Y (1997) Enzymological evidence for cannabichromenic acid biosynthesis. J Nat Prod 60:854-857

[8] Morimoto S, Komatsu K, Taura F, Shoyama Y (1998) Purification and characterization of cannabichromenic acid synthase from Cannabis sativa. Phytochemistry 49:1525-1529

[9] Vree T B, Breimer D D, Ginneken C A M van, Rossum J M van (1971) Identification of the methyl and propyl homologues of CBD, THC and CBN in hashish by a new method of combined gas chromatography-mass spectrometry. Acta Pharm Suedica 8:683-684

[10] Zeeuw R A de, Wijsbek J, Breimer D D, Vree T B, Ginneken C A van, Rossum J M van (1972) Cannabinoids with a propyl side chain in Cannabis. Occurrence and chromatographic behaviour. Science 175:778-779

[11] Raharjo T J, Chang W T, Choi Y H, Peltenburg-Looman A M G, Verpoorte R (2004b) Olivetol as a product of a polyketide synthase in Cannabis sativa L. Plant Science 166:381-385

[12] Samuelsson G (1999) Drugs of natural origin, 4$^{th}$ edition. Swedisch Pharmaceutical Press, Stockholm 551 pp

[13] Meijer E P M de (1995) Fibre hemp cultivars: a survey of origin, ancestry, availability and brief agronomic characteristics. J Int Hemp Association 2:66-73

[14] Virovets V G (1996) Selection for non-psychoactive hemp varieties (Cannabis sativa L.) in the CIS (former USSR). J Int Hemp Association 3:13-15

[15] Virovets V G, Scherban I, Orlov N (1997) Selektion auf niedrige Gehalt der Cannabinoid und hohe Produktivität im Schaffingsprogramm von Hanfsorten (Cannabis sativa L.), die keine narkotische Ativität besitzen. Proceedings of the symposium Bioresource Hemp 97, Frankfurt am Main, Germany. P 135-153

[16] Gorshkova L M, Senchenko G I, Virovets V G (1988) Method of evaluating hemp plants for content of cannabinoid compounds [Russian]. Referativnyi Zhurnal 12.65.322.

[17] Virovets V G (1998) Interview. J Int Hemp Association 5:32-34

[18] Virovets V G, Senchenko G I, Gorshkova L M, Sashko M M (1991) Narcotic activity of Cannabis sativa L. and prospects of its selection for decreased content of cannabinoids [Russian]. Agricultural Biology 1:35-49

[19] Pacifico D, Miselli F, Micheler M, Carboni A, Ranalli P, Mandolino G (2006) Genetics and marker-assisted selection of the chemotype in Cannabis sativa L. Molecular Breeding 17:257-268

[20] Sirikantaramas S, Taura F, Tanaka Y, Ishikawa Y, Morimoto S, Shoyama Y (2005) Tetrahydrocannabinolic acid synthase, the enzyme controlling marijuana psychoactivity, is secreted into the storage cavity of the glandular trichomes. Plant Cell Physiol 46:1578-1582

[21] Samuelsson G (1999) Drugs of natural origin, 4$^{th}$ edition. Swedisch Pharmaceutical Press, Stockholm 551 pp.

[22] Evans W C (2002) Pharmacognosy 15$^{th}$ edition. Saunders, Edinburgh, 585 pp.

[23] McPartland J M, Russo E B (2001) Cannabis and Cannabis extracts: greater than the sum of their parts? J. Cannabis Therapeutics 1:103-132.

[24] Williamson E M, Whalley B J (2002) Cannabis as a medicine: evidence for synergy. In: Medicinal uses of Cannabis, 26$^{th}$ LOF Symposium, Leiden.

[25] Speroni E, Govoni P, Grassi G, Utan A (2003) Antiinflammatory effects of Cannabis sativa L. extracts containing nonpsychoactive cannabinoids. In: Borrelli F, Capasso F, Milic N, Russo A (eds) Proceedings 3rd International Symposium on Natural Drugs, Indena, Naples, pp 107-114.

[26] Meijer E P M de, Hammond K M (2005) The inheritance of chemical phenotype in Cannabis sativa L. (II): cannabigerol predominant plants. Euphytica 145:189-198.

The invention claimed is:

1. An inbred reference Cannabis sativa plant characterized in that it:
 a) comprises stalked glandular trichomes having small dull heads free of white trichomes,
 b) does not express cannabinoids; yet expresses a profile of entourage compounds quantitatively substantially similar to a profile of entourage compounds of a comparator Cannabis sativa plant which expresses cannabinoids from which it has been bred, and
 c) comprises a cannabinoid knock out factor or monogenic mutation that blocks cannabinoid biosynthesis in Cannabis sativa governing a reaction in the pathway towards the phenolic moieties olivetolic and divarinic acid, wherein the source of said cannabinoid knock out factor or monogenic mutation is Cannabis sativa industrial hemp cultivar USO-31 deposited as NCIMB Accession number 42357.

2. A reference plant as claimed in claim 1 characterized in that a homogenized bulk extract exhibits a profile of entourage compounds which is quantitatively substantially similar to that of a comparator plant from which it has been bred.

3. A reference plant as claimed in claim 2 wherein the homogenised bulk extract has a % v/w oil yield of greater than 0.14%, more preferably greater than 0.2%, through 0.3% to 0.4% or more.

4. A reference plant as claimed in claim 1 characterised in that a homogenised bulk steam distilled extract comprises both monoterpenes and sesquiterpines.

5. A reference plant as claimed in claim 4 wherein the monoterpenes comprise at least myrcene, alpha pinene and beta pinene.

6. A reference plant as claimed in claim 5 wherein the myrcene, alpha pinene and beta pinene comprise at least 50%, through 60% to at least 70% of the monoterpenes detected.

7. A reference plant as claimed in claim 5 further comprising limonine and optionally linalol.

8. A reference plant as claimed in claim 7 further comprising cis- and/or trans-verbenol.

9. A reference plant as claimed in claim 4 wherein the sesquiterpenes comprise at least carophyllene and humulene.

10. A reference plant as claimed in claim 9 further comprising carophyllene oxide.

11. A reference plant as claimed in claim 9 in which humelene epoxide II is not detected.

12. A reference plant as claimed in claim 1 wherein the density of the stalked glandular trichomes is comparable to a cannabinoid producing plant.

13. A reference plant as claimed in claim 1 characterized in that it expresses monoterpenes, diterpenes, carotenoids, phytol and tetraterpenes.

14. A reference plant as claimed in claim 1 characterized in that it expresses sesquiterpenes, sterols and triterpenes.

15. A reference plant as claimed in claim 13 which expresses entourage compounds selected from one or more of: monoterpenes; sesquiterpenes; and flavonoids.

16. A reference plant as claimed in claim 1 having branching characteristic of a drug producing phenotype as opposed to a fibre producing phenotype.

17. A reference plant as claimed in claim 1 exhibiting vigour, characterized in that the total above ground dry weight is substantially equivalent to that of comparator drug producing plants.

18. A method of producing an inbred reference *Cannabis sativa* plant which comprises stalked glandular trichomes having small dull heads free of white trichomes and does not express cannabinoids yet generates a reference extract with a reference chemical profile which resembles that of a comparator plant less the cannabinoids comprising:
    a) selecting a plant which comprises a cannabinoid knock out factor or monogenic mutation that blocks cannabinoid biosynthesis in *Cannabis sativa* governing a reaction in the pathway towards the phenolic moieties olivetolic and divarinic acid, where the source of said cannabinoid knock out factor or monogenic mutation is *Cannabis sativa* industrial hemp cultivar USO-31 deposited as NCIMB Accession number 42357;
    b) selecting a therapeutically active comparator plant; and
    c) crossing the plants from (a) and (b) to obtain F1 progeny and self-crossing the F1 progeny to obtain an F2 progeny which is selected for the characteristics comprising stalked glandular trichomes having small dull heads free of white trichomes and does not express cannabinoids.

19. A method as claimed in claim 18 further comprising successive back crosses with a comparator plant to selectively breed for the desired characteristics.

20. A method of producing a designer plant extract comprising the steps of:
    i) obtaining an extract from the reference plant of claim 1; and
    ii) combining the extract of (i) with one or more cannabinoids.

* * * * *